United States Patent [19]

Frey et al.

[11] Patent Number: 4,581,337

[45] Date of Patent: Apr. 8, 1986

[54] POLYETHER POLYAMINES AS LINKING AGENTS FOR PARTICLE REAGENTS USEFUL IN IMMUNOASSAYS

[75] Inventors: William A. Frey; Donald M. Simons, both of Wilmington, Del.

[73] Assignee: E. I. Du Pont de Nemours and Company, Wilmington, Del.

[21] Appl. No.: 511,751

[22] Filed: Jul. 7, 1983

[51] Int. Cl.[4] .......................................... G01N 33/546
[52] U.S. Cl. .................................. 436/533; 436/534; 436/805; 436/823; 435/181
[58] Field of Search ............... 436/531, 532, 533, 534, 436/517, 543, 547, 805, 823; 435/180, 181; 427/2; 428/402, 403; 260/112 R

[56] References Cited

U.S. PATENT DOCUMENTS

| 4,064,080 | 12/1977 | Daniel | 260/8 |
|---|---|---|---|
| 4,181,636 | 1/1980 | Fischer | 260/8 |
| 4,210,723 | 7/1980 | Dorman et al. | 435/180 |
| 4,264,766 | 4/1981 | Fischer | 536/51 |
| 4,341,758 | 7/1982 | Sakakibara et al. | 424/12 |
| 4,401,765 | 8/1983 | Craig et al. | 436/533 |
| 4,480,042 | 10/1984 | Craig et al. | 436/533 |

OTHER PUBLICATIONS

Fear et al. (1958) Organic Fluorine Compounds, Part V, J. Chem. Soc. (London) 1322–1325.
Marvel et al. (1955) Organic Syntheses, Collective vol. 3, 366–367.

*Primary Examiner*—Robert J. Warden
*Assistant Examiner*—Cynthia Lee Foulke
*Attorney, Agent, or Firm*—George A. Frank

[57] ABSTRACT

Particle reagents, having polyether polyamine linking groups, for use in turbidimetric immunoassays are provided. These linking agents permit ready covalent attachment of compounds of biological interest to polymer particles and lead to immunoassays of improved precision.

11 Claims, No Drawings

POLYETHER POLYAMINES AS LINKING AGENTS FOR PARTICLE REAGENTS USEFUL IN IMMUNOASSAYS

TECHNICAL FIELD

This invention relates to particle reagents for use in turbidimetric immunoassays and, more particularly, to such reagents having hydrophilic polymeric linking groups for the attachment of compounds of biological interest to latex polymer particles

BACKGROUND ART

The agglutination reaction has long been used in visual (semi-quantitative) and quantitative assays for a wide variety of bacteria, cell-surface antigens, serum proteins and other analytes of clinical interest. Agglutination results from the reaction of bivalent antibodies with multivalent antigens of interest to produce aggregates which can be detected and/or measured in various ways. Similarly, the same reaction can be utilized for the detection of specific antibodies by the agglutination reaction caused by the addition of the corresponding antigen.

Generally, in order to produce large, cross-linked aggregates, the number of reactive sites on the antigens must be at least 2. When the detection of monovalent haptens is desired, the reaction scheme has to be modified as follows: a multivalent form of the antigen such as a hapten-protein conjugate is prepared and the free hapten present in a sample competes with its multivalent form for the available binding sites of the antibody, thereby reducing the amount of agglutination. This technique is referred to as inhibition of agglutination.

Production of multivalent forms of haptens is old in the art. Frequently, the hapten is bonded to a carrier protein as is done in the preparation of immunogens. The stoichiometry of the reaction can be adjusted to place three or more haptens per protein molecule, the exact number determined by the needs of the particular assay in which the material will be utilized.

Increased sensitivity to visual or instrumental detection of agglutination or its inhibition can be achieved by the use of particle reagents as carriers, rather than soluble proteins or protein conjugates. It has been shown, for example, that antiserum to hen ovalbumin was 2000-fold more sensitive in precipitating hen ovalbumin coated on colloidion particles than in precipitating hen albumin itself; H. N. Eisen, "Immunology", Harper and Row, 1974, page 394.

Antibody particle reagents are also known. A common method for preparation of such reagents is the adsorption of the antibodies onto the surface of suitable adsorbents. Polystyrene-based latex particles have been used extensively for this purpose. These reagents, however, are susceptible to desorption during storage or use leading to variations in reagent properties. This, in turn, can adversely affect assay sensitivity and reproducibility.

To overcome the problems of desorption, particle reagents can be prepared by covalent attachment of the compounds of biological interest to the surface of particles. Polystyrene polymers have been modified to include functional groups capable of covalent protein attachment. U.S. Pat. No. 4,064,080, issued Dec. 20, 1977, discloses styrene polymers with terminal aminophenyl groups and proteins attached to them. U.S. Pat. No. 4,181,636, issued Jan. 1, 1980, discloses carboxylated latex polymers coupled to immunologically active materials through a water soluble activating agent and their use as diagnostic reagents in agglutination tests. U.S. Pat. No. 4,210,723, issued July 1, 1980, describes shell-core latex polymer particles of 0.15–1.5 $\mu$m diameter having free epoxy groups on the surface of the particles and the coupling of proteins through these epoxy groups.

Other polymeric systems have also been developed for later attachment of immunologically active materials. U.S. Pat. No. 4,264,766, issued Apr. 28, 1981, discloses latex polymers having a particle size of 0.01–0.9 $\mu$m and having active groups such as carboxyl and amino groups to which water soluble polyhydroxy compounds can be attached covalently. Through the utilization of activating agents such as carbodiimides, immunologically active materials were attached to the latex particle/polyhydroxy compound carriers to form diagnostically useful reagents.

U.S. Pat. No. 4,401,765, issued Aug. 30, 1983 to Craig et al., discloses shell-core polymer particles wherein the inner core has a high refractive index resulting in high sensitivity to light scattering measurements and the outer shell contains functional groups to which compounds of biological interest can be attached directly or through a proteinaceous material Usually, low molecular weight compounds of biological interest (analytes) are not attached directly to latex particles. The reason for this is that such particle reagents often do not aggregate well when mixed with the appropriate antibody or that they lack functional groups appropriate for covalent attachment to the particle surface. To overcome these problems analytes are usually linked to particles via a bridge or spacer moiety.

The most commonly used spacers are proteins or glycoproteins, such as albumin. Human serum albumin (HSA) is a water-soluble protein having an abundance of amino groups which can be utilized in coupling to amino-reactive groups both on the analyte and on the particle surface.

Although particle reagents prepared from analyte-protein conjugates have shown great utility in general, there are still some disadvantages associated with their use. The solubility and stability characteristics of proteins limit the chemical means which can be used in forming the analyte-protein conjugate and attaching it to the particle. Proteins are denatured by extremes of temperature and pH and are frequently insoluble in organic solvents. Furthermore, even hydrophilic proteins have hydrophobic regions in which hydrophobic analytes can be buried. Extended storage of the particle reagent can result in protein hydrolysis, oxidation, conformational changes, and microbial degradation. Finally, the protein spacer can contain antigenic determinants which are recognized by antianalyte antibodies, resulting in nonspecific agglutination during an assay.

There is a need for hydrophilic, chemically well-defined linking groups which can be utilized in the preparation of particle reagents for use in clinical diagnostics.

DISCLOSURE OF INVENTION

The particle reagent of this invention consists essentially of:

(A) a polymer particle having an inner core and an outer shell wherein the inner core is a polymer having a refractive index of not less than 1.54 as measured at the wavelength of the sodium D line and wherein the outer shell is a polymer of
(1) an ethylenically unsaturated monomer having a functional group selected from the group consisting of epoxy, carboxy, and aldehyde, said functional group capable of reacting with a hydrophilic polymeric linker;
(2) optionally, other ethylenically unsaturated monomers in an amount sufficient to render the polymer particles substantially water insoluble; and
(3) not more than 10 parts by weight of the outer shell of the monomers of the inner core, said outer shell being formed by polymerization in the presence of said inner core; and wherein said polymer particle has an approximate diameter range of 0.03–0.1 μm and is covalently attached to
(B) a compound of biological interest through a hydrophilic polymeric linker of empirical formula:

$$H[NHC_2H_3R(OC_2H_3R)_xOC_2H_3R]_yNH_2$$

wherein R is H and/or methyl, x is 0–70 and y is 1–20.

The method of this invention for measuring compounds of biological interest comprises the steps
(A) incubating
(1) a particle reagent having high refractive index consisting essentially of:
(a) a polymer particle having an inner core and an outer shell wherein the inner core is a polymer having a refractive index of not less than 1.54 as measured at the wavelength of the sodium D line and wherein the outer shell is a polymer of
(i) an ethylenically unsaturated monomer having a functional group selected from the group consisting of epoxy, carboxyl, and aldehyde, said functional group capable of reacting with a hydrophilic polymeric linker;
(ii) optionally, other ethylenically unsaturated monomers in an amount sufficient to render the particle substantially water insoluble, and
(iii) not more than 10 parts by weight of the outer shell of the monomers of the inner core, said outer shell being formed by polymerization in the presence of said inner core; and wherein said polymer particle has an approximate diameter range of 0.03–0.1 μm; covalently attached to
(b) the compound of biological interest through said hydrophilic polymeric linker of empirical formula $$H[NHC_2H_3R(OC_2H_3R)_xOC_2H_3R]_yNH_2$$

wherein R is H and/or methyl, x is 0–70 and y is 1–20.
(2) a liquid suspected of containing the compound of biological interest; and
(3) an agglutinating agent; and
(B) photometrically measuring increased particle size resulting from agglutination.

The polyether-polyamine hydrophilic linkers of this invention are soluble in water and many organic solvents; are chemically and thermally stable; are resistant to microbial degradation; are not immunologically cross-reactive with anti-protein or anti-(hapten-carrier conjugate) antibodies; and possess no hydrophobic domains. Their substitution for proteins as linking agents also has the unexpected advantage of improving the precision of particle-based assays, reducing the amount of antibody required to achieve a desired level of signal and reducing the dependence of this assay on polyethylene ether glycol (PEG).

DESCRIPTION OF THE INVENTION

This invention relates to the preparation of improved particle reagents for use in turbidimetric immunoassays in which compounds of biological interest (analytes) are attached to high refractive index latex polymer particles via hydrophilic, polymeric linking agents.

The particle reagents are designed to maximize the sensitivity of the immunoassays by (1) being formed of a core material of high refractive index; (2) possessing a shell material which is capable of being covalently bound to polyether-polyamine hydrophilic linkers; and (3) being of a small particle size for optimal sensitivity in immunoassays. The linking agents are designed to be soluble in aqueous and organic solvents; chemically and thermally stable; chemically well-defined, i.e., reproducible; and capable of being attached covalently to amine-reactive groups on both the analyte and the particle surface.

The light scattering properties of particle suspensions depend on several variables, most importantly the particle size, the refractive indices of the core and the suspension medium, and the wavelength of light used for measurement. Thus, the selection of core material, particle size, and wavelength of detection of the agglutination reaction are all important factors in optimizing assay sensitivity. These factors can be determined by the type of light scattering detection means used.

For the turbidimetric detection of particle size change at a given wavelength of measurement, it is imperative that the particle size and refractive index be chosen with care since the turbidimetric signal goes through a maximum, producing a double-valued response with little or no sensitivity at the peak. In addition, the slope sensitivity is greater on the small particle size side of the peak than on the large and it increases with increasing refractive index ratio of particle to medium.

For these reasons, small particles of high refractive index and a short wavelength detection system are preferred for maximum sensitivity. There is a practical limit in the ultraviolet region for measurement of samples in serum because of light absorption by proteins and other components. Thus, convenient wavelengths are those in excess of approximately 320 nm. Longer wavelengths can be used with less sensitivity. Small particles, that is, those with a diameter of less than approximately 0.1 μm, are preferred because of both increased slope sensitivity and faster reaction rates. For reasons of stability and synthetic convenience, particle sizes greater than approximately 0.03 μm are preferred. In general, particle size range of 0.03–0.1 μm can be utilized in the particle reagent of this invention.

Several different methods of light scatter measurement can be utilized such as nephelometry, particle counting, quasi elastic light scattering, autocorrelation spectroscopy, and measurements of the dissymmetry or polarization of the particles. A preferred way of measurement of immunological reactions utilizing the particle reagents of this invention is by turbidity since no special equipment is required other than a spectrophotometer which is generally available in clinical laboratories. The spectrophotometer registers an apparent increased absorbance which is due to particle aggregates formed by the agglutination reaction. These aggregates scatter light out of the optical beam thus decreasing the amount of light reaching the detector. In practice, the apparent absorbance is an inverse measure of the agglutination inhibition caused by the analyte. To optimize the turbidity change which occurs during agglutination, it is important to select the particle size with care.

During the agglutination reaction, the effective particle size increases. For sensitive measurements, therefore, it is important to choose the wavelength at which the signal change for a given particle size change is optimal.

Because of the importance of the refractive index for turbidimetric detection of the agglutination reaction, core materials are restricted to those which will produce acceptable signal changes for the desired assay sensitivity. Thus, core polymers with high aromaticity and high atomic weight substituents are preferred over aliphatic polymers and, in general, polymers of high refractive indices are preferred over polymers with lower refractive indices.

The inner core of the polymer particles can be selected from a large group of materials with high refractive index. Preferred are those materials which can be prepared by emulsion polymerization in a manner so that the final particle size is controllable and is substantially uniform. Typical polymers utilized in the inner core of the polymer particles have refractive indices greater than 1.54 (at the Na D line, 569 nm). Since the refractive index is a function of wavelength, the scattering properties will be dependent upon the wavelength of measurement. In general, the refractive index is greater at shorter wavelengths. It is understood that the core polymer must not absorb light at the wavelength chosen for turbidimetric measurement.

The monomers of interest for the preparation of the inner core are those which contain vinyl or allyl groups in addition to substituents such as halides, aromatic, heterocyclic, unsaturated or carbocyclic groups which impart high refractivity.

Polymer particles useful for the preparation of the particle reagents of this invention can be prepared preferentially by emulsion polymerization. Staged emulsion polymerization can lead to core/shell polymers approximating the desired refractive index of not less than $n_D = 1.54$. To obtain a polymer of desired refractive index, it is preferred that the shell polymer not exceed approximately 10 parts by weight of the polymer particle.

A convenient way to control particle size of the polymer particles is to first prepare a seed emulsion whose particle size can be controlled by the amount of surfactant used. After preparation of the seed emulsion, additional monomer and surfactant can be added at a controlled rate to increase the size of the particles in the seed emulsion.

The outer shell polymer of the polymer particle can be prepared from a wide range of ethylenically unsaturated monomers having functional groups capable of reacting with the hydrophilic linking group to be attached. Optionally, the outer shell can also contain other ethylenically unsaturated monomers including the monomers used in preparing the inner core. The attachment of the shell polymer to the core can be accomplished by graft polymerization of the functional monomer to the residual ethylenically unsaturated groups in the core polymer or the functional monomer can be polymerized around the core to produce a contiguous shell. Preferred monomers include those containing an epoxy group such as glycidyl methacrylate, glycidyl acrylate, vinyl glycidyl ether, and methallyl glycidyl ether. Other functional groups include carboxyl and aldehyde.

It is preferable to carry the conversion of the core monomer(s) to substantial completion so that the shell polymer is a homopolymer or a copolymer of known composition rather than a copolymer of unknown composition Conversions in excess of 98% can be attained by increasing the temperature of the core emulsion to approximately 95° C. at the end of the polymerization. To further reduce the probability of producing a particle whose surface is a copolymer of unknown composition, the shell monomer can be added gradually rather than batchwise. In such a manner, the residual core monomer(s) can be consumed during the early stages of the shell polymer formation. When the monomer utilized is one which contains an epoxy group, it is preferred that the shell polymer be a homopolymer although, as a practical matter, monomers of the inner core, up to 10 parts by weight of the outer shell, can be present.

In the case of the shell monomers containing aldehyde or carboxylic acid groups, care must be taken to avoid the formation of water soluble polymers. Thus, for example, acrolein or methacrylic acid cannot be utilized alone to form a homopolymer shell structure. They can be copolymerized, however, with other monomers to produce water-insoluble polymer particles.

The outer shell is preferably a homopolymer but can contain not more than 10 parts, preferably not more than 5 parts, and even more preferably not more than 2 parts, by weight of the outer shell of the monomers of the inner core. These monomers can be the residual monomers from the polymerization of the inner core or any other suitable ethylenically unsaturated monomer.

The particle reagents can contain several different functional shell materials A preferred one contains epoxy groups which can be conveniently utilized for the covalent attachment of compounds of biological interest via the hydrophilic, polymeric linking agents. The particle reagents so formed are the subject of the instant invention.

There can be two methods of preparing a particle reagent which contains a compound of biological interest, the analyte, covalently attached through the hydrophilic polymeric linkers. The linker can first be attached to the polymer particle and the compound of biological interest or a suitable derivative of the analyte can then be attached to the linker. Suitable derivatives are those containing functional groups that can react with amines in aqueous media under relatively mild conditions, for example, epoxide, aldehyde or carboxyl groups. The functional groups in the analyte derivative can be the same or different from those present in the latex polymer particle shell. Thus, both the derivative and the particle shell can contain carboxyl groups or the derivative can contain a carboxyl group and the particle shell an epoxide group. Substitution of the polyether polyamines of this invention for the proteins often employed as linking agents requires no drastic departure from conventional procedures. A limitation of this method is that all steps are necessarily carried out in a substantially aqueous environment.

Alternatively, the compound of biological interest or its suitable derivative is first attached to the hydrophilic linker followed by the attachment of this product to the particle. If necessary, the reaction of the analyte derivative with the polyether polyamine linker can now be carried out in any suitable solvent under vigorous conditions, since the polyether amines are soluble in many organic solvents, are oxidatively and thermally stable, and are not readily degraded by acidic or basic catalysts. Thus, analyte derivatives unsuitable for use in an aqueous medium can now be used. For example, one can use analyte derivatives containing, for example, acid halide, acid anhydride, allylic halide, α-haloketone, sulfonyl halide or sulfonate ester groupings to prepare an analyte-linker product. This can then be reacted in an aqueous medium with latex polymer particles having amine-reactive groups by procedures well known in the art. The analyte-linker products, sometimes called conjugates, however, can be coupled to the polymer particles at more alkaline pH values than is the case with the prior art analyte-protein conjugates. This degree of freedom frequently results in improved reaction of the conjugate with the particle surface.

The surface coverage of the polymer particle by analyte conjugate, that is the ratio of the polymer particles to compounds of biological interest, can be varied by stoichiometry, by reaction time, and by dilution of the compounds of biological interest with an inactive diluent. While complete coverage can yield fast agglutination rates, lesser surface coverage can be important in increasing assay sensitivity.

The polyether polyamines of this invention have the following empirical formula:

$$H[NHC_2H_3R(OC_2H_3R)_xOC_2H_3R]_yNH_2$$

wherein R can be H, $CH_3$ and, depending on the method of preparation of the starting glycol, both H and $CH_3$ (such as when the product is derived from propylene oxide-capped polyethylene glycol), x is 0–70 and y is 1–20. Preferred are x=1–30, more preferred x=1–15, with the most preferred in some cases being x=1–2; while preferred y=1–10, most preferred y=1–5. Those products in which R=H (polyethylene ether polyamines), will be referred to as PEPA while those in which R=$CH_3$ (polypropylene ether polyamines), will be referred to as PPPA.

It should be understood that the above formula is presented for the sake of convenience. In those cases where R=$CH_3$, it is contemplated that the position of the R group in the formula is not fixed but can be on either of the neighboring carbon atoms depending on the type of starting glycol or oxide and on the nature of the reaction conditions utilized in preparing the polyether polyamine.

The polyether polyamines utilized in this invention are prepared by reacting ammonia with the di(p-toluenesulfonate) ester of the appropriate polyalkylene ether glycol (hereafter referred to as the ditosylate ester) having a number average molecular weight ($\overline{M}_n$) in the range of, for example, 150 to 3000 (for R=H), $\overline{M}_n$ being calculated from the hydroxyl number of the glycol. The stoichiometry, solvent, and reaction conditions are chosen so that the primary amine formed in the early stages of the reaction by displacement of tosylate groups by ammonia is itself able to compete in the displacement of additional tosylate groups, resulting in a condensation polymerization to give the desired products. The resultant polyether polyamines can be used as pure compounds or as the oligomeric mixtures produced in the reaction. Furthermore, the polyether chain segments within the polyether polyamines can be monodisperse, that is, x has a single discrete value or they can be polydisperse, in which case x signifies an overall average chain length.

The preferred solvent for the ammonia-ditosylate ester reaction is pure, anhydrous, inhibitor-free tetrahydrofuran (THF). The reaction is preferably carried out for 4 hours at 100° C. under autogenous pressure in a sealed stainless steel reactor. The by-product ammonium tosylate is insoluble in THF and is removed by filtration of the cold reaction mixture.

The degree of condensation polymerization, given by the value y and shown by the subscript following (S—NH) in the formulae in Table I, is regulated by the ratio of ammonia to ditosylate ester and by the concentration of the reactants. The oligomeric products can be characterized by the total basic nitrogen content as determined by acid titration. Table IA shows the theoretical nitrogen content of specific polyether amine oligomers as a function of the $\overline{M}_n$ of the polyethylene ether glycol (PEG, calculated from hydroxyl number values), or of x calculated from $\overline{M}_n$, from which the prerequisite ditosylate ester was derived, while Table IB shows similar data based on monodisperse PEGs (S represents the appropriate polyethylene ether segment):

TABLE I

THEORETICAL NITROGEN CONTENT OF POLYETHER POLYAMINE OLIGOMERS

| | Nitrogen content (meq/g) | | | | | | | | | | |
|---|---|---|---|---|---|---|---|---|---|---|---|
| | A | | | | | | | | B | | |
| | | | | | | | | | PEG— | | |
| PEG—$\overline{M}_n$ molecular weight | 160 | 200 | 390 | 595 | 800 | 1000 | 1300 | 2700 | $HO(CH_2CH_2O)_3H$ 150.2 | $HO(CH_2CH_2O)_4H$ 194.2 | $HO(CH_2CH_2O)_5H$ 283.3 |
| -x | 1.2 | 2.1 | 6.45 | 11.1 | 15.8 | 20.3 | 27.1 | 58.95 | 1 | 2 | 3 |
| Polyether polyamine | | | | | | | | | | | |
| $H_2N—$(S—NH)H | 12.7 | 10.1 | 5.15 | 3.37 | 2.51 | 2.00 | 1.54 | 0.74 | 13.5 | 10.4 | 7.83 |
| $H_2N—$(S—NH)$_2$H | 10.0 | 7.91 | 3.95 | 2.57 | 1.90 | 1.52 | 1.16 | 0.56 | 10.7 | 8.17 | 6.08 |
| $H_2N—$(S—NH)$_3$H | 9.09 | 7.14 | 3.54 | 2.29 | 1.69 | 1.35 | 1.04 | 0.50 | 9.74 | 7.37 | 5.47 |
| $H_2N—$(S—NH)$_4$H | 8.60 | 6.75 | 3.33 | 2.15 | 1.59 | 1.27 | 0.97 | 0.47 | 9.23 | 6.97 | 5.15 |
| $H_2N—$(S—NH)$_{10}$H | 7.71 | 6.02 | 2.95 | 1.90 | 1.40 | 1.12 | 0.86 | 0.41 | 8.28 | 6.22 | 4.58 |

TABLE I-continued

THEORETICAL NITROGEN CONTENT OF
POLYETHER POLYAMINE OLIGOMERS

| | | | | | | | | | | | |
|---|---|---|---|---|---|---|---|---|---|---|---|
| $H_2N-$(S—NH)H | 7.09 | 5.52 | 2.70 | 1.74 | 1.28 | 1.02 | 0.78 | 0.37 | 7.62 | 5.70 | 4.20 |

Table II shows experimentally obtained values of nitrogen contents for mixtures of oligomers derived from polyethylene ether glycols having $\overline{M}_n$ of 200 and 595, respectively. (In all cases the components were heated together for 4 hours at 100° C. under autogenous pressure.) Although the values in Table II represent average nitrogen contents of complex mixtures of oligomers, it is apparent that decreasing the ammonia/ditosylate ratio and increasing the ditosylate concentration favor the condensation polymerization process. The physical properties of the products also reflect this. For example, the viscosity of the products was found to increase substantially in going from D to G, D being a viscous liquid and G being a waxy solid at room temperature.

TABLE II

NITROGEN CONTENT OF OLIGOMERS DERIVED FROM
PEG ($\overline{M}_n$ = 200) AND PEG ($\overline{M}_n$ = 595)
AS AFFECTED BY STOICHIOMETRY

| $\overline{M}_n$ of PEG starting material | 200 | | | 595 | | | |
|---|---|---|---|---|---|---|---|
| | A | B | C | D | E | F | G |
| PEG ditosylate (moles) | 0.13 | 0.13 | 0.13 | 0.082 | 0.082 | 0.082 | 0.082 |
| THF(ml) | 500 | 250 | 125 | 500 | 250 | 125 | 65 |
| Anhydrous $NH_3$ (moles) | 11.7 | 2.9 | 1.5 | 11.7 | 5.9 | 2.9 | 1.5 |
| Nitrogen content (meq/g) | 7.0 | 6.0 | 5.2 | 2.7 | 2.6 | 2.46 | 2.0 |

The polyethylene ether polyamines described above are synthesized from polyethlene ether ditosylates which are themselves synthesized from the appropriate polyethylene ether glycols by reaction with p-toluenesulfonyl chloride (tosyl chloride) in the presence of an acid acceptor. Preferred acid acceptors are tertiary amines.

Fear et al. [J. Chem. Soc. (London), 1322-1325 (1958)] synthesized triethyleneether ditosylate and tetraethylene ditosylate, using a modification of the procedure described by Marvel et al. [*Organic Syntheses*, Collective Volume 3, 366-367 (1955)]. This procedure utilizes pyridine as both acid acceptor and solvent and is thus present in very high concentration. The polyether polyamines prepared from ditosylate esters synthesized by the above method, when utilized in preparing the particle reagents of this invention, afforded particle reagents that did not perform well in various turbidimetric immunoassays. The reason for this is believed to be the presence of high concentrations of pyridine which can lead to various side reactions substantially diminishing the quality of the ditosylate ester.

The preferred procedure for synthesizing the polyethylene ether ditosylates used in this invention employs methylene chloride as a solvent and triethylamine as an acid acceptor. Special care is taken to remove excess triethylamine from the product. Polyether polyamines prepared from these ditosylates yielded particle reagents that performed well in turbidimetric immunoassays.

Certain PPPA products are available commercially under the trade name Jeffamine from the Texaco Chemical Company.

The particle reagents prepared with the polyether polyamines can be suspended in a substantially aqueous medium which can further contain buffer, serum components and surfactants to yield a monodispersed particle reagent for use in light scattering immunoassays.

The present invention is further concerned with an immunologically active, stable particle reagent for use in sensitive light scattering immunoassays for measuring compounds of biological interest. The types of assays include a wide variety of substances in biological fluids, cell and tissue extracts for which an immunological counter reactant can be produced. The compounds of biological interest include serum, plasma, salivary, urinary or milk proteins, drugs, vitamins, hormones, enzymes, antibodies, polysaccharides, bacteria, protozoa, fungi, viruses, cell and tissue antigens and other blood cell or blood fluid substances.

The immunoassay can be designed in a variety of ways depending on the type of analyte and the sensitivity required.

For analytes in relatively high concentration such as certain serum proteins, appropriate antibody particle reagents can be used in a direct particle enhanced turbidimetric immunoprecipitation assay. The method of this invention provides increased detectability over conventional immunoprecipitation techniques, reduces reagent costs, and allows the use of smaller patient sample volumes. Conversely, for the detection of circulating antibodies of interest, the counter reactive antigen or antibody particle reagent can be used in a direct assay. In either case, the antigen or antibody is covalently attached to the particle via a polyether polyamine linking agent.

The inhibition immunoassay method of this invention also requires, in addition to the particle reagent, a bi- or multifunctional agent, hereinafter referred to as an agglutinating agent to cause the agglutination of the particle reagent. It is this agglutination which can be inhibited by the compound of biological interest. The agglutinating agent can be an antibody to the compound of biological interest or a particle reagent based on a polymer particle, as described above, covalently attached to an antibody to the compound of biological interest via a polyether polyamine.

The agglutinating agent can also be a multivalent conjugate of the compound of biological interest and a polyether polyamine. Such a conjugate can be utilized in situations where the particle reagent utilized in the method of this invention contains a covalently attached antibody to the compound of biological interest.

Several different assay configurations can be utilized for the measurement of analytes. In one such configuration, antigenic particle reagents can be prepared from the analyte or a suitable analyte derivative, a polyether polyamine and polymer particles, and the inhibition of the reaction of these particles with antibodies by free analyte is determined. The reaction can be performed by direct competition between the particle reagent and the analyte for the antibody or by sequential reaction in which analyte is first reacted with excess antibody followed by addition of the antigen particle reagent to react with the excess antibody.

In another assay configuration, both antibody and antigen particle reagents can be present, of the same or different sizes, and the inhibition by analyte can be performed in a competitive or sequential mode. Either the antibody or the antigen particle reagent or both can employ a polyether polyamine linking agent.

The particle-enhanced turbidimetric immunoassays of this invention are generally carried out in an aqueous, buffered medium which can additionally contain surfactants, preservatives, and polyethylene glycol. In some cases, it can also be desirable to add a reducing agent, such as dithioerythritol (DTE) in order to reduce serum interferences. The assay can be performed manually or it can be adapted to a variety of automated or semi-automated instruments.

When the assay of this invention is compared to other particle-enhanced turbidimetric assays such as that described in U.S. Pat. No. 4,401,765, issued Aug. 30, 1983 to Craig et al., employing HSA as linking agent between analyte and particle, several unexpected advantages result from the use of a polyether polyamine linker.

One such advantage is that the antibody requirement of the assay is reduced approximately ten-fold. Since antibodies are frequently difficult and expensive to prepare, this reduction in the amount needed to achieve a given level of signal can represent a significant cost savings. Another advantage is that the amount of PEG required in the assay to achieve the same level of signal is reduced approximately by a factor of two. The concentration of PEG actually required varies depending on the chain length of the polyether polyamine linker. Appropriately chosen polyether polyamine reduces the amount of PEG and simplifies the adaptation of the assay to many automated clinical analysis instruments in which reagent volumes are limited.

There exists an interrelationship between the amount of antibody required in the assay and the amount of PEG required. Additional reduction in antibody requirement can be achieved by increasing the amount of PEG in the assay. Some such increase can now be accommodated since the use of the polyether polyamine linkers led to a reduction in PEG requirements.

A totally unexpected and surprising additional advantage was demonstrated by an approximately four-fold improvement in assay precision when a polyether polyamine (PEPA) linker was utilized over an assay utilizing particle reagents having an HSA linker. Such improvement in precision resulting from the use of the synthetic linker over the protein linker is highly significant since good precision, as measured by the coefficient of variation, is essential to the success of any immunoassay.

In the Examples below, illustrating the invention, all parts are by weight unless otherwise indicated.

EXAMPLE 1

THEOPHYLLINE ASSAY

A. Synthesis of Ditosylate Ester of Polyethylene Ether Glycol

A 3-liter, 3-necked flask, equipped with mechanical stirrer, thermometer, addition funnel, and a system for maintaining a dry nitrogen atmosphere, was cooled in an ice-water bath and flushed with dry nitrogen. The system was maintained under a slight positive nitrogen pressure throughout the reaction. Tosyl chloride (343.2 g, 1.8 moles) was placed in the flask followed by 1200 mL of methylene chloride. After a slightly endothermic dissolution, polyethylene ether glycol (Sigma Chemical Co., 150.0 g, 0.750 mole, $\overline{M}_n = 200$ by hydroxyl number) was rapidly added and the container rinsed with 150 mL of methylene chloride. Triethylamine (191.2 g, 1.89 moles) was then added dropwise in 1 hr. while the temperature was maintained at 15°–18° C. The triethylamine container and addition funnel were rinsed with 150 mL of methylene chloride. The reaction mixture was stirred for the rest of the day at 15°–20° C. and allowed to stand overnight at the same temperature. Triethylamine hydrochloride precipitated throughout the course of the reaction.

About 24 hours after the reaction was started, the mixture was cooled in an ice-bath, stirred for one hour to induce separation of any additional triethylamine hydrochloride, and filtered into a chilled filter flask. The filtrate was extracted first with a chilled solution of hydrochloric acid (32 mL of concentrated HCl in 500 mL of water), then twice with 500-mL portions of chilled water. The methylene chloride solution was dried over anhydrous sodium sulfate (250 g), the solution decanted from the drying agent and the methylene chloride evaporated in a flash evaporator (at no time was the temperature of the product permitted to exceed 35° C.). To insure removal of all traces of methylene chloride, the residue was dissolved in 200 mL of pure, anhydrous, inhibitor-free tetrahydrofuran and then the solvent was removed in the flash evaporator under the same conditions.

B. Preparation of the Polyether Polyamine (PEPA)

Polyethylene ether ditosylate from (A) above, 228 g, was dissolved in 1500 mL of pure, anhydrous, inhibitor-free tetrahydrofuran and the solution was placed in a stainless-steel autoclave. The autoclave was sealed and anhydrous ammonia (600 g) was pumped in. The stirred mixture was heated to 100° C. and held at this temperature for 4 hours under autogeneous pressure. The autoclave was cooled to room temperature and the pressure released slowly. The polyether polyamine-THF solution contained crystalline ammonium tosylate and ammonium chloride, products of residual tosyl chloride [from (A)] and ammonia. The solids were removed by filtration and the THF evaporated in a flash evaporator.

The residue was added to 4-times its weight of cold water and the mixture chilled in ice for approximately 1 hr. Para-toluenesulfonamide separated as a copious precipitate. The mixture was filtered and activated carbon (Darco G-60) in amount equal to ¼ the weight of the original residue added. The aqueous mixture was heated to boiling with occasional stirring, allowed to cool to room temperature, and then filtered through diatomaceous earth in order to remove the carbon. The water was removed in a flash evaporator at a bath temperature of 60°–70° C. The amine content of the residue, as determined by acid titration, was 6.8 meq/g, corresponding to $x=2.1$ and y of approximately 4 (see Table IA).

C. Preparation of Theophylline-Polyether Polyamine Conjugate

N-Ethyl-N'-(3-dimethylaminopropyl)carbodiimide hydrochloride (260 mg) was added to a solution of 8-(3-carboxypropyl)-1,3-dimethylxanthine (Peninsula Labs, 340 mg) in dimethylsulfoxide (30 mL), and the solution stirred for 3 hours at 23° C. The polyether polyamine from (B) above (1.13 g, 7.7 meq of amine) in 20 mL of dimethylsulfoxide was added and stirring was continued for an additional 18 hours at 23° C. The solution of the conjugate so obtained was stored at 4° C.

D. Preparation of Theophylline-Polyether Polyamine-Particle Reagent

Theophylline-PEPA conjugate solution from (C) above (27 mL) was mixed with 5 mM sodium phosphate (450 mL, pH 8.0) and 5.4 mL of 0.15 M phosphate buffer containing 10% GAFAC RE 610 (an anionic surfactant available from GAF Corp.). The pH was adjusted to 10.0–10.1 by addition of 0.2 M and 0.02 M sodium hydroxide. A polymer particle latex (17% solids; 64.8 mL), prepared according to Example 4 of U.S. Pat. No. 4,401,765, issued Aug. 30, 1983 to Craig et al., containing epoxy-functional particles, was then added and the mixture was heated at 70° C. with stirring for 2 hours.

The reaction mixture was cooled, 600 mL of 15 mM phosphate buffer containing 0.1% GAFAC RE 610 (pH 7.0) was added, and centrifuged in six portions for 16 hours at 8,000 rpm. The supernatant liquid was decanted and each pellet resuspended by sonicating in 15 mM phosphate buffer containing 0.1% GAFAC (200 mL, pH 7.0); centrifuged again at 13,000 rpm for 6.5 hours; the supernatant liquid decanted; and each pellet resuspended in 50 mL of the final buffer (15 mM phosphate containing 0.35% GAFAC and 0.01% thimerosal). Each sample was sonicated for 3 minutes to produce monodisperse particle suspensions. The six samples were mixed together, brought to a final volume of 450 mL, and filtered through a 0.8μ filter.

E. Assay

The assay was performed on the aca ™ discrete clinical analyzer (available from E. I. du Pont de Nemours and Company, Wilmington, Del.) in analytical test packs (described in Pat. No. Re. 29,725, issued Aug. 8, 1978 to Johnson, et al., which is hereby incorporated by reference). Forty μL of pooled human serum containing a known concentration of theophylline between 0 and 40 μg/mL was automatically injected into a test pack in the filling station of the instrument, followed by 4.96 mL of 0.15 M phosphate buffer, pH 7.8. PEG 8000 (65.0 mg; providing a 1.3% final concentration), 5.8 mg DTE, 0.05 mL GAFAC RE-610 solution (10% w/v in distilled water), and 0.06 mL of particle reagent from (D) above were added to the pack in breaker/mixer I. Three and one-half minutes later the reaction was initiated at breaker/mixer II by the addition of 2 μL of anti-theophylline antibody (diluted 1:24 with 10 mg/mL HSA, 1 M NaCl, 0.05 M K$_2$HPO$_4$, 0.1% (w/v) NaN$_3$, and 0.002% (w/v) thimerosal, pH 7.8). The antibody was a mouse monoclonal antibody to theophylline designated 30/15 (obtained from a hybridoma cell line, ATCC accession number HB8152) and was used as sterile-filtered ascites fluid; its production is described in copending patent application Ser. No. 406,554 filed Aug. 9, 1982 which is hereby incorporated by reference. The rate of change in turbidity, as a function of particle aggregation, was recorded as the difference in absorbance at 340 nm measured 29 and 46 seconds after antibody addition. The data are shown in Table III below.

TABLE III

| INHIBITION OF TURBIDITY BY THEOPHYLLINE | |
|---|---|
| Theophylline (μg/mL) | Rate (mA/min at 340 nm) |
| 0 | 220 |
| 2.5 | 186 |
| 5.0 | 148 |
| 10.0 | 87 |
| 20.0 | 43 |
| 40.0 | 18 |

EXAMPLE 2

COMPARISON OF ASSAY PERFORMANCE UTILIZING THEOPHYLLINE-HSA PARTICLE REAGENT AND THEOPHYLLINE-PEPA PARTICLE REAGENT

A particle enhanced turbidimetric inhibition immunoassay using theophylline-HSA particle reagent was performed as described in Example 1(E) above except that the sample size was 20 μL; the final concentration of PEG was 3%, and 28 μL of undiluted antibody was added at breaker/mixer II.

Table IVA compares the precision (% C.V. in μg/ml, 20-pack mean) obtained using a polyether polyamine linker of this invention versus the HSA linker. Precision was improved approximately four-fold at both the 10 μg/mL and the 20 μg/mL theophylline levels by using the linker of this invention.

Table IVB compares the rate of change in turbidity at 340 nm in a theophylline assay using the different linking agents. In addition to the fourteen-fold reduction in the amount of antibody needed, both the total signal and the separation are better with the particle reagents of this invention than with the HSA particles.

TABLE IV

| A. PRECISION | | |
|---|---|---|
| | % C.V. (μg/mL) | |
| Theophylline (μg/mL) | PEPA Particles | HSA Particles |
| 10 | 2.3 | 9.0 |
| 20 | 1.4 | 6.0 |
| B. INHIBITION OF TURBIDITY | | |
| THEOPHYLLINE (μg/mL) | PEPA PARTICLES (Rate, mA/min at 340 nm) | HSA PARTICLES (Rate, mA/min at 340 nm) |
| 0 | 220 | 156 |

TABLE IV-continued

| | | |
|---|---|---|
| 2.5 | 186 | 144 |
| 5.0 | 148 | 125 |
| 10.0 | 87 | 85 |
| 20.0 | 43 | 50 |
| 40.0 | 18 | 32 |

EXAMPLE 3

THEOPHYLLINE ASSAYS

A series of polyether polyamines (PEPA) was Prepared from polyethylene ether glycols of various molecular weights according to the procedure described in Example 1. These polyether polyamines were then used to prepare theophylline particle reagents as described in Example 1.

The assay of Example 1(E) was repeated except that 3 µL of antibody was used instead of 2 µL; DTE was eliminated; and PEG and GAFAC were added with the buffer in the filling station of the instrument. Table V shows the final concentration of PEG 8000 required in the assay for maximum signal at the zero calibrator level as a function of the molecular weight of the starting glycol. At the low and high ends of the molecular weight range, more PEG was required in assays using the synthetic linker particle reagents than using the HSA linker. When the starting glycol had an $\overline{M}_n$ of 150 or 200 (x=1 and, 2.1, respectively), however, the PEG requirement was reduced by a factor of 2. At intermediate molecular weights ($\overline{M}_n$=390 or 595), the PEG requirement was approximately the same. (Appropriate x and y values can be established from Tables IA and IB from the known $\overline{M}_n$ values and the nitrogen content, in meq/g sample, of the various PEPA preparations given in Table V. Nitrogen content was determined by acid titration; any impurities in a sample decrease the analyzed nitrogen value from the theoretical, resulting in higher apparent y values. For this reason, values for y so calculated are approximate and are the upper limit for any sample.)

TABLE V
EFFECT OF PEPA ON PEG CONCENTRATION
IN THEOPHYLLINE ASSAY

| Starting Polyethylene Ether Glycol ($\overline{M}_n$) | Nitrogen Content (meq/g) | y | % PEG (approximate) for maximum activity |
|---|---|---|---|
| 106 | — | 1[(1)] | >4.0 |
| 150 | 9.3 | 4 | 1.5 |
| 200 | 6.8 | 4 | 1.5 |
| 390 | 3.7 | 3 | 3.0 |
| 595 | 2.7 | 2 | 3.0 |
| 1300 | 0.93 | 4 | 4.0 |
| 2730 | 0.49 | 4 | >6.0 |

[(1)]Commercially available 2,2'-diaminoethyl ether, x = 0.

EXAMPLE 4

THEOPHYLLINE ASSAY

A. Preparation of Theophylline-Polypropylene Ether Polyamine Conjugate

N-(3-Dimethylaminopropyl)-N'-ethyl carbodiimide hydrochloride (453 mg) was added to a solution of 8-(3-carboxypropyl)-1,3-dimethylxanthine (Peninsula Labs, 592 mg) in dimethylsulfoxide (44 mL), and the solution stirred for 3 hours at 23° C. The polypropylene ether polyamine (JEFFAMINE D-230, Texaco Chemical Co., 1.562 g) in 44 mL of dimethylsulfoxide was added and stirring was continued for an additional 18 hours at 23° C. The solution of the conjugate so obtained was stored at 4° C.

B. Preparation of Theophylline-Polypropylene Ether Polyamine-Particle Reagent

Theophylline-PPPA conjugate solution from (A) above (90 mL) was mixed with 5 mM sodium phosphate (1500 mL, pH 8.0) containing 0.12% GAFAC RE-610 (an anionic surfactant available from GAF Corp.). The pH was adjusted to 10.0-10.1 by addition of 0.2 M sodium hydroxide. The mixture was heated to 70° C. and a polymer particle latex 216 mL), prepared according to Example 4 of U.S. Pat. No. 4,401,765, issued Aug. 30, 1983 to Craig et al., containing epoxy-functional particles, was then added with stirring for 2 hours.

The reaction mixture was cooled, diluted with 1500 mL of 15 mM sodium phosphate (pH 7.0) containing 0.1% GAFAC RE-610, and filtered using both a 100 micron and a 3 micron filter. The mixture was ultrafiltered to remove unreacted conjugate using a high-performance hollow fiber ultrafiltration system (Amicon Corporation, Model DC10EM) and 15 mM sodium phosphate (60 L, pH 7.0) containing 0.1% GAFAC RE-610. The latex suspension was brought to a final volume of 1500 mL.

C. Assay

The assay was performed on the aca™ discrete clinical analyzer in analytical test packs (described in Pat No. Re. 29,725, issued Aug. 8, 1978 to Johnson, et al.). Forty µL of pooled human serum containing known concentration of theophylline between 0 and 40 µg/mL was automatically injected into a test pack in the filling station of the instrument, followed by 4.96 mL of 0.15 M phosphate buffer, pH 7.8. PEG 8000 (55 mg), 6.0 mg dithioerythritol, 60 µL GAFAC RE-610 solution (16.7% w/v in distilled water), and 52.4 µL of particle reagent from (B) above were added to the pack in breaker/mixer I. Three and one-half minutes later the reaction was initiated at breaker/mixer II by the addition of 3.48 µL of anti-theophylline antibody solution described in Example 1 above (prepared by diluting 1 part mouse ascites fluid with 24 parts of a solution containing 10 mg/mL HSA, 1M NaCl, 0.05 M $K_2HPO_4$, 0.1% (w/v) $NaN_3$, and 0.002% (w/v) thimerosal, pH 7.8).

The rate of change in turbidity, as a function of particle aggregation, was recorded as the difference in absorbance at 340 nm measured 29 and 46 seconds after antibody addition. The data are shown in Table VI below.

TABLE VI
INHIBITION OF TURBIDITY BY THEOPHYLLINE

| Theophylline (µg/mL) | Rate (mA/min at 340 nm) |
|---|---|
| 0 | 213 |
| 2.5 | 172 |
| 5.0 | 119 |
| 10.0 | 77 |
| 20.0 | 38 |
| 40.0 | 18 |

EXAMPLE 5

COMPARISON OF ASSAY PERFORMANCE UTILIZING THEOPHYLLINE-HSA PARTICLE REAGENT AND THEOPHYLLINE-PPPA PARTICLE REAGENT

A particle-enhanced turbidimetric inhibition immunoassay using theophylline-HSA particle reagent was performed as described in Example 4 except that the sample size was 20 μL, the final concentration of PEG was 3% and 28 μL of undiluted antibody was added at breaker/mixer II.

Table VII compares the precision (% C.V. in μg/mL, 20-pack mean) obtained using the polypropylene ether polyamine linker of this invention versus the HSA linker. Precision was improved approximately 2-3-fold by using the linker of this invention.

TABLE VII

| | PRECISION % C.V. (μg/mL) | |
|---|---|---|
| Theophylline (μg/mL) | PPPA Particles | HSA Particles |
| 10 | 2.6 | 9.0 |
| 20 | 3.2 | 6.0 |

We claim:

1. A particle reagent consisting essentially of:
   (A) a polymer particle having an inner core and an outer shell wherein the inner core is a polymer having a refractive index of not less than 1.54 as measured at the wavelength of the sodium D line and wherein the outer shell is a polymer of
      (1) an ethylenically unsaturated monomer having a functional group selected from the group consisting of epoxy, carboxy, and aldehyde, said functional group capable of reacting with a hydrophilic polymeric linker; and
      (2) not more than 10 parts by weight of the outer shell of the monomers of the inner core, said outer shell being formed by polymerization in the presence of said inner core; and wherein said polymer particle has an approximate diameter range of 0.03–0.1 μm and is covalently attached to
   (B) a compound of biological interest through a hydrophilic polymeric linker of empirical formula:

$H[NHC_2H_3R(OC_2H_3R)_xOC_2H_3R]_yNH_2$ wherein R is at least one member selected from the group consisting of H and $CH_3$, x is 0–70 and y is 1–20.

2. The particle reagent of claim 1 wherein said outer shell additionally contains other ethylenically unsaturated monomers in an amount sufficient to render the polymer particles substantially water insoluble.

3. The particle reagent of claim 1 or claim 2 wherein R=H.

4. The particle reagent of claim 3 wherein X=1–15 and y=1–15.

5. The particle reagent of claim 4 wherein X=1–2 and y=1–5.

6. The particle reagent of claim 1 or claim 2 wherein the linker is derived from propylene oxide-capped polyethylene glycol.

7. The particle reagent of claim 1 or claim 2 wherein X=1–15 and y=1–15.

8. A method for measuring compounds of biological interest comprising the steps of:
   (A) incubating
      (1) a particle reagent having high refractive index consisting essentially of:
         (a) a polymer particle having an inner core and an outer shell wherein the inner core is a polymer having a refractive index of not less than 1.54 as measured at the wavelength of the sodium D line and wherein the outer shell is a polymer of
            (i) an ethylenically unsaturated monomer having a functional group selected from the group consisting of epoxy, carboxyl, and aldehyde, said functional group capable of reacting with a hydrophilic polymeric linker; and
            (ii) not more than 10 parts by weight of the outer shell of the monomers of the inner core, said outer shell being formed by polymerization in the presence of said inner core; and wherein said polymer particle has an approximate diameter range of 0.03–0.1 μm; covalently attached to
         (b) the compound of biological interest through a hydrophilic polymeric linker of empirical formula $H[NHC_2H_3R(OC_2H_3R)_xOC_2H_3R]_yNH_2$ wherein R is at least one member selected from the group consisting of H and $CH_3$, x is 0–70 and y is 1–20,
      (2) a liquid suspected of containing the compound of biological interest; and
      (3) an agglutinating agent; and
   (B) photometrically measuring increased particle size resulting from agglutination.

9. The particle reagent of claim 9 wherein said outer shell additionally contains other ethylenically unsaturated monomers in an amount sufficient to render the polymer particles substantially water insoluble.

10. The method of claim 8 or claim 9 wherein R=H.

11. The method of claim 10 wherein X=1–15 and y=1–15.

* * * * *